United States Patent
Wang et al.

(10) Patent No.: US 12,258,357 B2
(45) Date of Patent: Mar. 25, 2025

(54) TRIFLUOROACETYL IODIDE COMPOSITIONS USEFUL FOR MAKING TRIFLUOROIODOMETHANE

(71) Applicant: Honeywell International Inc., Charlotte, NC (US)

(72) Inventors: Haiyou Wang, Amherst, NY (US); Haridasan K. Nair, Williamsville, NY (US); Daniel C. Merkel, Orchard Park, NY (US); Selma Bektesevic, Williamsville, NY (US); Terris Yang, East Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 18/400,050

(22) Filed: Dec. 29, 2023

(65) Prior Publication Data

US 2024/0166677 A1    May 23, 2024

Related U.S. Application Data

(63) Continuation of application No. 17/495,506, filed on Oct. 6, 2021, now abandoned.

(60) Provisional application No. 63/091,725, filed on Oct. 14, 2020.

(51) Int. Cl.
*C07F 13/00* (2006.01)

(52) U.S. Cl.
CPC .................. *C07F 13/00* (2013.01)

(58) Field of Classification Search
CPC ........ C07C 17/363; C07C 19/16; C07F 13/00
See application file for complete search history.

(56) References Cited

U.S. PATENT DOCUMENTS

| | | | |
|---|---|---|---|
| 5,532,411 A * | 7/1996 | Braun | C07C 51/60 560/231 |
| 5,892,136 A | 4/1999 | Nagasaki et al. | |
| 7,132,578 B1 | 11/2006 | Mukhopadhyay et al. | |
| 7,196,236 B2 | 3/2007 | Mukhopadhyay et al. | |
| 2012/0190892 A1 | 7/2012 | Saint-Jalmes et al. | |

(Continued)

FOREIGN PATENT DOCUMENTS

| | | |
|---|---|---|
| CN | 103524325 A | 1/2014 |
| CN | 107176902 A | 9/2017 |

OTHER PUBLICATIONS

International Search Report and Written Opinion issued in International Application No. PCT/US/2021/071841, mailed Feb. 3, 2022, 8 pages.

*Primary Examiner* — Jafar F Parsa
(74) *Attorney, Agent, or Firm* — Faegre Drinker Biddle & Reath LLP

(57) ABSTRACT

The present disclosure provides a composition including trifluoroacetyl iodide, at least one organic impurity and at least one inorganic impurity. The at least one organic impurity includes at least one of: difluoroiodomethane, pentafluoroiodoethane, iodomethane, iodopropane, dichlorotetrafluoroethane, dichlorotrifluoroethane, trichlorotrifluoroethane, methyltrifluoroacetate, trifluoroacetic anhydride, difluorobutane and methyl propane. The at least one inorganic impurity includes at least one of: hydrogen iodide, hydrogen chloride, iodine and hydrogen triiodide.

27 Claims, 2 Drawing Sheets

(56) References Cited

U.S. PATENT DOCUMENTS

2020/0062679 A1\* 2/2020 Nair .......................... B01J 35/19
2022/0112226 A1   4/2022 Wang et al.

\* cited by examiner

TRIFLUOROACETYL IODIDE COMPOSITIONS USEFUL FOR MAKING TRIFLUOROIODOMETHANE

CROSS REFERENCE TO RELATED APPLICATIONS

This application is a continuation application of U.S. patent application Ser. No. 17/495,506, filed Oct. 6, 2021, which claims priority to Provisional Application No. 63/091,725, filed Oct. 14, 2020, both of which are herein incorporated by reference in their entireties.

FIELD

The present disclosure relates to trifluoroacetyl iodide compositions. Specifically, the present disclosure relates to trifluoroacetyl iodide compositions useful for producing trifluoroiodomethane.

BACKGROUND

Trifluoroiodomethane ($CF_3I$), also known as perfluoromethyliodide, trifluoromethyl iodide, or iodotrifluoromethane, is a useful compound in commercial applications as a refrigerant or a fire suppression agent, for example. Trifluoroiodomethane is a low global warming potential molecule with negligible ozone depletion potential. Trifluoroiodomethane can replace more environmentally damaging materials.

Methods of preparing trifluoroacetyl iodide are known. For example, the article, "The Reactions of Metallic Salts of Acids with Halogens. Part I. The Reaction of Metal Trifluoroacetates with Iodine, Bromine, and Chlorine," R. N. Haszeldine, *Journal of the Chemical Society*, pp. 584-587 (1951), describes a batch reaction of trifluoroacetyl chloride and anhydrous hydrogen iodide without a catalyst for 8 hours at 120° C. to produce trifluoroacetyl iodide at a yield of about 62%.

U.S. Pat. No. 7,196,236 (Mukhopadhyay et al.) discloses a catalytic process for producing trifluoroiodomethane using reactants comprising a source of iodine, at least a stoichiometric amount of oxygen, and a reactant $CF_3R$, where R is selected from the group consisting of —COOH, —COX, —CHO, —COOR$_2$, AND —SO$_2$X, where R$_2$ is alkyl group and X is a chlorine, bromine, or iodine. Hydrogen iodide, which may be produced by the reaction, can be oxidized by the at least a stoichiometric amount of oxygen, producing water and iodine for economic recycling.

U.S. Pat. No. 7,132,578 (Mukhopadhyay et al.) also discloses a catalytic, one-step process for producing trifluoroiodomethane from trifluoroacetyl chloride. However, the source of iodine is iodine fluoride (IF). In contrast to hydrogen iodide, iodine fluoride is relatively unstable, decomposing above 0° C. to $I_2$ and $IF_5$. Iodine fluoride may also not be available in commercially useful quantities.

Commercial methods of preparing trifluoroiodomethane ($CF_3I$) from trifluoroacetyl iodide ($CF_3COI$) are known. For example, co-pending U.S. patent application Ser. No. 16/549,412 discloses processes for producing trifluoroiodomethane from trifluoroacetyl iodide, as well as a process for producing trifluoroacetyl iodide. The disclosed processes are high-yielding, gas-phase processes and use starting materials that are relatively inexpensive and readily available in commercial quantities.

Compositions of trifluoroacetyl iodide are needed that allow more economical operation because the production of trifluoroiodomethane from trifluoroacetyl iodide may be subject to undesirable side reactions.

SUMMARY

The present disclosure provides compositions including trifluoroacetyl iodide ($CF_3COI$), at least one organic impurity and at least one inorganic impurity that are suitable for the manufacture trifluoroiodomethane ($CF_3I$).

In one embodiment, the present invention provides a composition comprising trifluoroacetyl iodide, at least one organic impurity comprising at least one of: difluoroiodomethane, pentafluoroiodoethane, iodomethane, iodopropane, dichlorotetrafluoroethane, dichlorotrifluoroethane, trichlorotrifluoroethane, methyltrifluoroacetate, trifluoroacetic anhydride, difluorobutane and methyl propane, and at least one inorganic impurity comprising at least one of: hydrogen iodide, hydrogen chloride, iodine and hydrogen triiodide.

The above mentioned and other features of the disclosure, and the manner of attaining them, will become more apparent and will be better understood by reference to the following description of embodiments.

DETAILED DESCRIPTION

Figure 1:
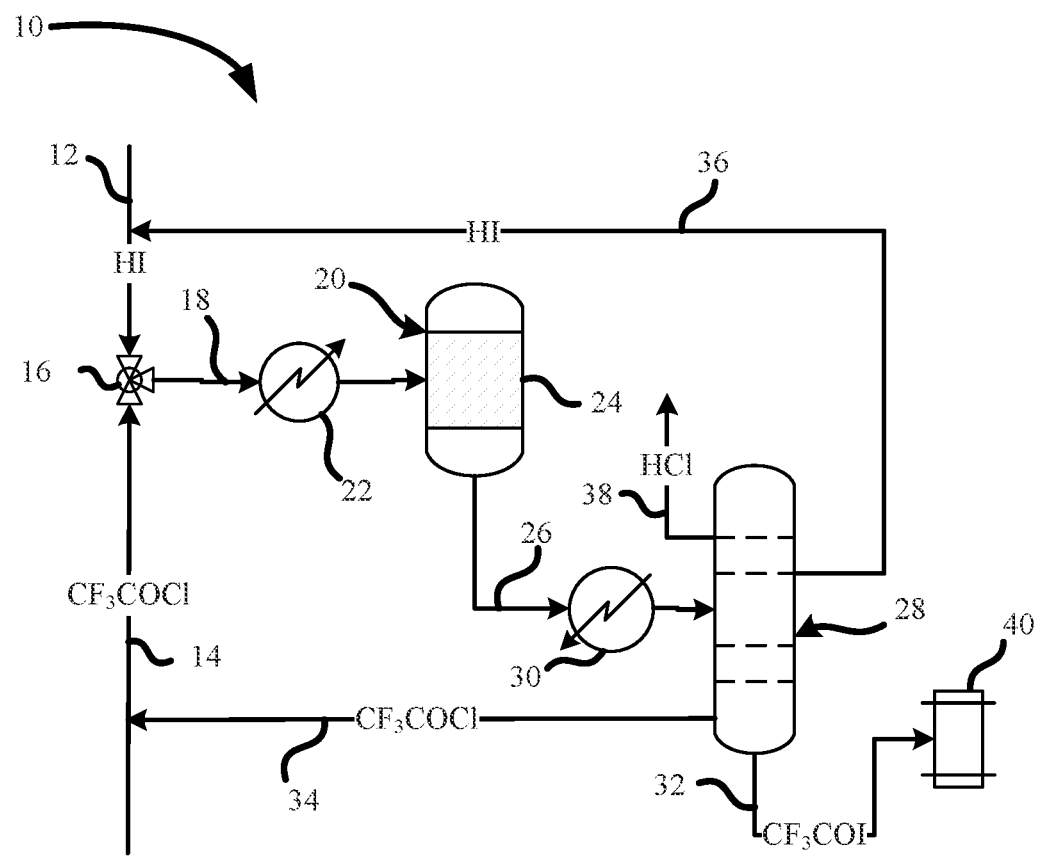
FIG. 1 is a process flow diagram showing a gas-phase process for manufacturing trifluoroacetyl iodide compositions.

The present disclosure describes trifluoroacetyl iodide compositions including at least one impurity organic impurity and at least one inorganic impurity. Even with the impurities, the compositions have been found to be suitable for the manufacture of trifluoroiodomethane.

The manufacture of trifluoroiodomethane ($CF_3I$) from trifluoroacetyl iodide ($CF_3COI$) can take place in a vapor phase reactor according to Equation 1 below:

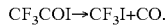    Eq. 1:

$$CF_3COI \rightarrow CF_3I + CO.$$

In the manufacture of trifluoroiodomethane according to Equation 1, the trifluoroacetyl iodide is provided as a composition including organic and inorganic impurities because pure trifluoroacetyl iodide can be too costly to permit the economically efficient manufacture of trifluoroiodomethane. It has been found that some impurities can have a more detrimental impact on the overall efficiency of process than other impurities. For example, it is believed that some hydrogen-containing impurities and some halogen-containing impurities in the trifluoroacetyl iodide composition can result in increased formation of byproducts, such as methyl trifluoride ($CF_3H$) and iodine ($I_2$). The production of these byproducts comes at the expense of the production of the desired trifluoroiodomethane product. Examples of hydrogen-containing impurities include trifluoroacetic acid (TFA), hydrogen iodide (HI), hydrogen chloride (HCl) and hydrogen triiodide ($HI_3$). Examples of halogen-containing impurities include trifluoroacetyl fluoride ($CF_3COF$), trifluoroacetyl chloride ($CF_3COCl$), difluoroiodomethane ($CF_2HI$), pentafluoroiodoethane ($CF_3CF_2I$), iodomethane ($CH_3I$), iodine ($I_2$), iodopropane ($C_3H_7I$) and trifluoroiodomethane ($CF_3I$). While the trifluoroiodomethane is the desired product, trifluoroiodomethane in the trifluoroacetyl iodide composition feeding the reaction can react to produce undesired byproducts.

It is also believed that increased concentrations of some iodine-containing impurities, such as iodine ($I_2$) and hydrogen triiodide ($HI_3$), can cause increased corrosion of processing equipment. The increased corrosion can reduce the useful lifetime of the processing equipment.

In contrast, it has been found that some other organic impurities in the trifluoroacetyl iodide composition have relatively little effect on the efficiency of the process. Such impurities generally pass through the reactor without reacting and do not corrode the processing equipment. Examples of such organic impurities include dichlorotetrafluoroethane ($C_2Cl_2F_4$), dichlorotrifluoroethane ($C_2HCl_2F_3$), chlorotrifluoroethane ($C_2H_2ClF_3$), trichlorotrifluoroethane ($C_2Cl_3F_3$), methyltrifluoroacetate ($CF_3COOCH_3$), trifluoroacetic anhydride (($CF_3CO)_2O$), difluorobutane ($C_4H_8F_2$) and methyl propane ($CH_3CH(CH_3)CH_3$).

Trifluoroacetyl iodide compositions useful as a feed stock for producing trifluoroiodomethane according to the process of Equation 1 above include trifluoroacetyl iodide, at least one organic impurity comprising at least one of: difluoroiodomethane, pentafluoroiodoethane, iodomethane, iodopropane, dichlorotetrafluoroethane, dichlorotrifluoroethane, trichlorotrifluoroethane, methyltrifluoroacetate, trifluoroacetic anhydride, difluorobutane and methyl propane, and at least one inorganic impurity comprising at least one of: hydrogen iodide, hydrogen chloride, iodine and hydrogen triiodide.

The organic compounds in the trifluoroacetyl iodide compositions may be measured by gas chromatography (GC) and gas chromatography-mass spectroscopy (GC-MS) analyses. Peak areas provided by the GC analysis for each of the organic compounds can be combined to provide a GC area percentage (GC area %) of the total organic compounds for each of the organic compounds as a measurement of the relative concentrations of the organic compounds in the compositions. The GC area % may be interpreted as equivalent to a weight %.

The concentration of organic impurities in the trifluoroacetyl iodide compositions, in GC area % of total organic compounds, may be as low as about 0.05%, about 0.1%, about 0.5%, or about 1% or may be as high as about 2%, about 3%, about 4%, or about 5%, or within any range defined between any two of the foregoing values, such as about 0.05% to about 5%, about 0.1% to about 4%, about 0.5% to about 3%, about 1% to about 2%, about 0.05% to about 2%, about 0.5% to about 2%, about 2% to about 5%, or about 0.05% to about 1%, for example. Preferably, the concentration of inorganic impurities in the trifluoroacetyl iodide compositions, in GC area % of total organic compounds, may be from about 0.05% to about 3%. More preferably, the concentration of inorganic impurities in the trifluoroacetyl iodide compositions, in GC area % of total organic compounds, may be from about 0.05% to about 2%. Most preferably, the concentration of inorganic impurities in the trifluoroacetyl iodide compositions, in GC area % of total organic compounds, may be from about 0.05% to about 1%.

The concentration of difluoroiodomethane, iodopropane, dichlorotetrafluoroethane, dichlorotrifluoroethane, difluorobutane and methyl propane in total in the trifluoroacetyl iodide compositions, in GC area % of total organic compounds, may be as low as about 0.0001%, about 0.001%, about 0.005%, about 0.01%, about 0.02% or about 0.03%, or may be as high as about 0.05%, about 0.1%, about 0.2%, about 0.3% or about 0.5%, or within any range defined between any two of the foregoing values, such as about 0.0001% to about 0.5%, about 0.001% to about 0.3%, about 0.005% to about 0.2%, about 0.01% to about 0.1%, about 0.001% to about 0.2%, about 0.001% to about 0.03%, about 0.05% to about 0.5%, or about 0.1% to about 0.3%, for example.

The concentration of trifluoroacetic anhydride when present in the trifluoroacetyl iodide compositions, in GC area % of total organic compounds, may be as low as about 0.001%, about 0.005%, about 0.01%, about 0.02% or about 0.03%, or may be as high as about 0.05%, about 0.1%, about 0.2%, about 0.3%, about 0.5% or about 1%, or within any range defined between any two of the foregoing values, such as about 0.001% to about 1%, about 0.005% to about 0.5%, about 0.01% to about 0.3%, about 0.02% to about 0.2%, about 0.03% to about 0.1%, about 0.01% to about 0.05%, about 0.1% to about 1%, or about 0.01% to about 0.3%, for example.

The concentration of pentafluoroiodoethane when present in the trifluoroacetyl iodide compositions, in GC area % of total organic compounds, may be as low as about 0.0001%, about 0.001%, about 0.005%, about 0.01%, about 0.02% or about 0.03%, or may be as high as about 0.05%, about 0.1%, about 0.2%, about 0.3% or about 0.5%, or within any range defined between any two of the foregoing values, such as about 0.0001% to about 0.5%, about 0.001% to about 0.3%, about 0.005% to about 0.2%, about 0.01% to about 0.1%, about 0.001% to about 0.2%, about 0.001% to about 0.03%, about 0.05% to about 0.5%, or about 0.1% to about 0.3%, for example. Preferably, the concentration of pentafluoroiodoethane in the trifluoroacetyl iodide compositions, in GC area % of total organic compounds, is from about 0.0001% to about 0.2%. More preferably, the concentration of pentafluoroiodoethane in the trifluoroacetyl iodide compositions, in GC area % of total organic compounds, is from about 0.0001% to about 0.1%. Most preferably, the concentration of pentafluoroiodoethane in the trifluoroacetyl iodide compositions, in GC area % of total organic compounds, is from about 0.0001% to about 0.05%.

The concentration of iodomethane when present in the trifluoroacetyl iodide compositions, in GC area % of total organic compounds, may be as low as about 0.0001%, about 0.001%, about 0.005%, about 0.01%, about 0.02% or about 0.03%, or may be as high as about 0.05%, about 0.1%, about 0.2%, about 0.3% or about 0.5%, or within any range defined between any two of the foregoing values, such as about 0.0001% to about 0.5%, about 0.001% to about 0.3%, about 0.005% to about 0.2%, about 0.01% to about 0.1%, about 0.001% to about 0.2%, about 0.001% to about 0.03%, about 0.05% to about 0.5%, or about 0.1% to about 0.3%, for example. Preferably, the concentration of iodomethane in the trifluoroacetyl iodide compositions, in GC area % of total organic compounds, is from about 0.0001% to about 0.2%. More preferably, the concentration of iodomethane in the trifluoroacetyl iodide compositions, in GC area % of total organic compounds, is from about 0.0001% to about 0.1%. Most preferably, the concentration of iodomethane in the trifluoroacetyl iodide compositions, in GC area % of total organic compounds, is from about 0.0001% to about 0.05%.

The concentration of methyltrifluoroacetate, when present, in the trifluoroacetyl iodide compositions, in GC area % of total organic compounds, may be as low as about 0.001%, about 0.005%, about 0.01%, about 0.02%, about 0.03% or about 0.05%, or may be as high as about 0.1%, about 0.2%, about 0.3%, about 0.5%, about 1%, or about 2%, or within any range defined between any two of the foregoing values, such as about 0.001% to about 2%, about 0.005% to about 1%, about 0.01% to about 0.5%, about 0.02% to about 0.3%, about 0.03% to about 0.2%, about 0.05% to about 0.1%, about 0.1% to about 1%, or about 0.02% to about 0.1%, for example.

Any of the trifluoroacetyl iodide compositions described above may further include at least one additional organic impurity comprising at least one of: trifluoroacetic acid, trifluoroacetyl fluoride, trifluoroacetyl chloride, trifluoroiodomethane and chlorotrifluoroethane.

The concentration of trifluoroacetic acid when present in the trifluoroacetyl iodide compositions, in GC area % of total organic compounds, may be as low as about 0.001%, about 0.005%, about 0.01%, about 0.02%, about 0.03% or about 0.05%, or may be as high as about 0.1%, about 0.2%, about 0.3%, about 0.5%, about 1%, or about 2%, or within any range defined between any two of the foregoing values, such as about 0.001% to about 2%, about 0.005% to about 1%, about 0.01% to about 0.5%, about 0.02% to about 0.3%, about 0.03% to about 0.2%, about 0.05% to about 0.1%, about 0.1% to about 1%, or about 0.02% to about 0.1%, for example. Preferably, the concentration of trifluoroacetic acid in the trifluoroacetyl iodide compositions, in GC area % of total organic compounds, is from about 0.001% to about 1%. More preferably, the concentration of trifluoroacetic acid in the trifluoroacetyl iodide compositions, in GC area % of total organic compounds, is from about 0.001% to about 0.5%. Most preferably, the concentration of trifluoroacetic acid in the trifluoroacetyl iodide compositions, in GC area % of total organic compounds, is from about 0.001% to about 0.2%.

The concentration of trifluoroacetyl fluoride when present in the trifluoroacetyl iodide compositions, in GC area % of total organic compounds, may be as low as about 0.0001%, about 0.0005%, about 0.001%, about 0.002% or about 0.003%, or may be as high as about 0.005%, about 0.01%, about 0.02%, about 0.03% or about 0.05%, or within any range defined between any two of the foregoing values, such as about 0.0001% to about 0.05%, about 0.0005% to about 0.03%, about 0.001% to about 0.02%, about 0.002% to about 0.01%, about 0.003% to about 0.005%, about 0.0005% to about 0.02%, about 0.005% to about 0.05%, or about 0.001% to about 0.01%, for example. Preferably, the concentration of trifluoroacetyl fluoride in the trifluoroacetyl iodide compositions, in GC area % of total organic compounds, is from about 0.0001% to about 0.02%. More preferably, the concentration of trifluoroacetyl fluoride in the trifluoroacetyl iodide compositions, in GC area % of total organic compounds, is from about 0.0001% to about 0.01%. Most preferably, the concentration of trifluoroacetyl fluoride in the trifluoroacetyl iodide compositions, in GC area % of total organic compounds, is from about 0.0001% to about 0.005%.

The concentration of trifluoroacetyl chloride when present in the trifluoroacetyl iodide compositions, in GC area % of total organic compounds, may be as low as about 0.001%, about 0.005%, about 0.01%, about 0.02%, about 0.03% or about 0.05%, or may be as high as about 0.1%, about 0.2%, about 0.3%, about 0.5%, about 1%, or about 2%, or within any range defined between any two of the foregoing values, such as about 0.001% to about 2%, about 0.005% to about 1%, about 0.01% to about 0.5%, about 0.02% to about 0.3%, about 0.03% to about 0.2%, about 0.05% to about 0.1%, about 0.1% to about 1%, or about 0.02% to about 0.1%, for example. Preferably, the concentration of trifluoroacetyl chloride in the trifluoroacetyl iodide compositions, in GC area % of total organic compounds, is from about 0.001% to about 1%. More preferably, the concentration of trifluoroacetyl chloride in the trifluoroacetyl iodide compositions, in GC area % of total organic compounds, is from about 0.001% to about 0.5%. Most preferably, the concentration of trifluoroacetyl chloride in the trifluoroacetyl iodide compositions, in GC area % of total organic compounds, is from about 0.001% to about 0.2%.

The concentration of trifluoroiodomethane when present in the trifluoroacetyl iodide compositions, in GC area % of total organic compounds, may be as low as about 0.0001%, about 0.001%, about 0.01%, about 0.02% or about 0.05%, or may be as high as about 0.1%, about 0.5%, about 1%, or about 2% or within any range defined between any two of the foregoing values, such as about 0.0001% to about 2%, about 0.001% to about 1%, about 0.01% to about 0.5%, about 0.02% to about 0.1%, about 0.001% to about 0.05%, about 0.1% to about 0.5%, about 0.05% to about 0.3%, or about 0.001% to about 0.03%, for example. Preferably, the concentration of trifluoroiodomethane in the trifluoroacetyl iodide compositions, in GC area % of total organic compounds, is from about 0.0001% to about 1%. More preferably, the concentration of trifluoroiodomethane in the trifluoroacetyl iodide compositions, in GC area % of total organic compounds, is from about 0.0001% to about 0.5%. Most preferably, the concentration of trifluoroiodomethane in the trifluoroacetyl iodide compositions, in GC area % of total organic compounds, is from about 0.0001% to about 0.1%.

The concentration of chlorotrifluoroethane when present in the trifluoroacetyl iodide compositions, in GC area % of total organic compounds, may be as low as about 0.0001%, about 0.001%, about 0.005%, about 0.01%, about 0.02% or about 0.03%, or may be as high as about 0.05%, about 0.1%, about 0.2%, about 0.3% or about 0.5%, or within any range defined between any two of the foregoing values, such as about 0.0001% to about 0.5%, about 0.001% to about 0.3%, about 0.005% to about 0.2%, about 0.01% to about 0.1%, about 0.001% to about 0.2%, about 0.001% to about 0.03%, about 0.05% to about 0.5%, or about 0.1% to about 0.3%, for example.

The concentration of iodine ($I_2$) in the trifluoroacetyl iodide compositions may be measured via titration, as is known in the art. The concentration of hydrogen iodide, hydrogen chloride, hydrogen triiodide and other hydrogen-containing inorganic compounds may be measured by H-NMR, as is known in the art.

The concentration of inorganic impurities in the trifluoroacetyl iodide compositions, may be as low as about 0.01 weight percent (wt. %), about 0.02 wt. %, about 0.03 wt. % or about 0.05 wt. %, or as high as about 0.1 wt. %, about 0.2 wt. %, about 0.3 wt. %, about 0.5 wt. %, about 1 wt. %, or about 1.5 wt. %, or within any range defined between any two of the foregoing values, such as about 0.01 wt. % to about 1.5 wt. %, about 0.02 wt. % to about 1 wt. %, about 0.03 wt. % to about 0.5 wt. %, about 0.05 wt. % to about 0.3 wt. %, about 0.02 wt. % to about 0.2 wt. %, about 0.01 wt. % to about 0.05 wt. %, about 0.1 wt. % to about 1 wt. %, or about 0.1 wt. % to about 0.5 wt. %, for example. Preferably, the concentration of inorganic impurities in the trifluoroacetyl iodide compositions is from about 0.01 wt. % to about 0.5 wt. %. More preferably, the concentration of inorganic impurities in the trifluoroacetyl iodide compositions is from about 0.01 wt. % to about 0.1 wt. %. Most preferably, the concentration of inorganic impurities in the trifluoroacetyl iodide compositions is from about 0.01 wt. % to about 0.05 wt. %.

The concentration of hydrogen iodide when present in the trifluoroacetyl iodide compositions, may be as low as about 0.0001 wt. %, 0.001 wt. %, about 0.005 wt. %, about 0.01 wt. %, about 0.02 wt. %, or about 0.03 wt. %, or as high as about 0.05 wt. %, about 0.1 wt. %, about 0.2 wt. %, about 0.3 wt. % or about 0.5 wt. %, or within any range defined between any two of the foregoing values, such as about 0.0001 wt. % to about 0.5 wt. %, about 0.001 wt. % to about 0.5 wt. %, about 0.005 wt. % to about 0.3 wt. %, about 0.01 wt. % to about 0.2 wt. %, about 0.02 wt. % to about 0.1 wt. %, about 0.03 wt. % to about 0.05 wt. %, about 0.01 wt. % to about 0.3 wt. %, about 0.005 wt. % to about 0.03 wt. %, about 0.05 wt. % to about 0.5 wt. %, or about 0.05 wt. % to about 0.3 wt. %, for example. Preferably, the concentration of hydrogen iodide in the trifluoroacetyl iodide compositions is from about 0.0001 wt. % to about 0.3 wt. %. More preferably, the concentration of hydrogen iodide in the trifluoroacetyl iodide compositions is from about 0.0001 wt. % to about 0.1 wt. %. Most preferably, the concentration of hydrogen iodide in the trifluoroacetyl iodide compositions is from about 0.0001 wt. % to about 0.05 wt. %.

The concentration of iodine ($I_2$) when present in the trifluoroacetyl iodide compositions, may be as low as about 0.001 wt. %, about 0.005 wt. %, about 0.01 wt. %, about 0.02 wt. %, or about 0.03 wt. %, or as high as about 0.05 wt. %, about 0.1 wt. %, about 0.2 wt. %, about 0.3 wt. % or about 0.5 wt. %, or within any range defined between any two of the foregoing values, such as about 0.001 wt. % to about 0.5 wt. %, about 0.005 wt. % to about 0.3 wt. %, about 0.01 wt. % to about 0.2 wt. %, about 0.02 wt. % to about 0.1 wt. %, about 0.03 wt. % to about 0.05 wt. %, about 0.01 wt. % to about 0.3 wt. %, about 0.005 wt. % to about 0.03 wt. %, about 0.05 wt. % to about 0.5 wt. %, or about 0.05 wt. % to about 0.3 wt. %, for example. Preferably, the concentration of iodine in the trifluoroacetyl iodide compositions is from about 0.001 wt. % to about 0.3 wt. %. More preferably, the concentration of iodine in the trifluoroacetyl iodide compositions is from about 0.001 wt. % to about 0.1 wt. %. Most preferably, the concentration of iodine in the trifluoroacetyl iodide compositions is from about 0.001 wt. % to about 0.05 wt. %.

The concentration of hydrogen triiodide when present in the trifluoroacetyl iodide compositions, may be as low as about 0.0001 wt. %, about 0.001 wt. %, about 0.005 wt. %, about 0.01 wt. %, about 0.02 wt. %, or about 0.03 wt. %, or as high as about 0.05 wt. %, about 0.1 wt. %, about 0.2 wt. %, about 0.3 wt. % or about 0.5 wt. %, or within any range defined between any two of the foregoing values, such as about 0.0001 wt. % to about 0.05 wt. %, about 0.001 wt. % to about 0.5 wt. %, about 0.005 wt. % to about 0.3 wt. %, about 0.01 wt. % to about 0.2 wt. %, about 0.02 wt. % to about 0.1 wt. %, about 0.03 wt. % to about 0.05 wt. %, about 0.01 wt. % to about 0.3 wt. %, about 0.005 wt. % to about 0.03 wt. %, about 0.05 wt. % to about 0.5 wt. %, or about 0.05 wt. % to about 0.3 wt. %, for example. Preferably, the concentration of hydrogen triiodide in the trifluoroacetyl iodide compositions is from about 0.0001 wt. % to about 0.3 wt. %. More preferably, the concentration of hydrogen triiodide in the trifluoroacetyl iodide compositions is from about 0.0001 wt. % to about 0.1 wt. %. Most preferably, the concentration of hydrogen triiodide in the trifluoroacetyl iodide compositions is from about 0.0001 wt. % to about 0.05 wt. %.

FIG. 1 is a process flow diagram showing an exemplary gas-phase process 10 for manufacturing trifluoroacetyl iodide. The trifluoroacetyl iodide may be produced by processes other than those described below. As shown in FIG. 1, the process 10 comprises material flows of hydrogen iodide (HI) 12 and trifluoroacetyl chloride ($CF_3COCl$) 14. Although trifluoroacetyl chloride is used to illustrate the processes of FIG. 1, it is understood that trifluoroacetyl bromide or trifluoroacetyl fluoride may be used instead of trifluoroacetyl chloride. The flow of hydrogen iodide 12 and the flow of trifluoroacetyl chloride 14 are combined in a mixer valve 16 to form a reactant stream 18. The reactant stream 18 may be provided directly to a reactor 20. Alternatively, the reactant stream 18 may pass through a preheater 22 to heat the reactant stream 18 before the reactant stream 18 is provided to the reactor 20.

The trifluoroacetyl chloride and the hydrogen iodide in the reactant stream 18 react in the presence of a catalyst 24 contained within the reactor 20 to produce a product stream 26 comprising trifluoroacetyl iodide ($CF_3COI$) and various organic and inorganic impurities, including unreacted trifluoroacetyl chloride and hydrogen iodide.

The product stream 26 may proceed directly to a distillation column 28. Alternatively, the product stream 26 may pass through a heat exchanger 30 before the product stream 26 is provided to the distillation column 28, as shown in FIG. 1. The heat exchanger 30 is configured to cool the product stream 26 before it enters the distillation column 28. The distillation column 28 is configured for the separation of some of the by-products, reactants, and organic compounds from the trifluoroacetyl iodide to produce a purified product stream 32. As shown in FIG. 1, the distillation column 28 can be configured to separate and return the unreacted hydrogen iodide to the flow of hydrogen iodide 12 for use in the reactant stream 18 in a hydrogen iodide flow 36 and to separate and return the unreacted trifluoroacetyl chloride to the flow of trifluoroacetyl chloride 14 for use in the reactant stream 18 in a trifluoroacetyl chloride flow 34. The distillation column 28 can also be configured to separate the hydrogen chloride into a hydrogen chloride stream 38 for sale, reuse elsewhere, or disposal. The purified product stream 32 directed to a storage tank 40 comprises a trifluoroacetyl iodide composition as described above. The purified product stream 32 may be further purified before being directed to the storage tank 40.

Figure 2:
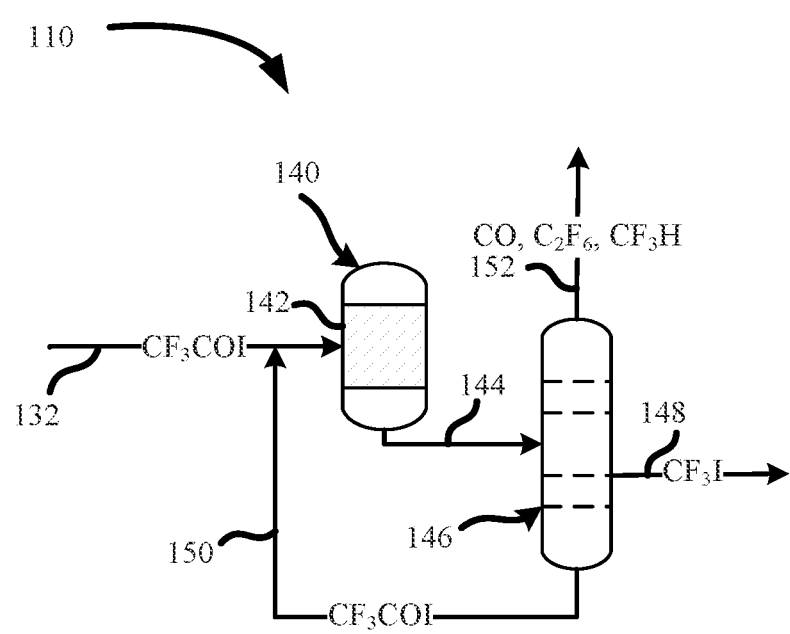
FIG. 2 is a process flow diagram showing a gas-phase process for manufacturing trifluoroiodomethane from trifluoroacetyl iodide compositions.

FIG. 2 is a process flow diagram showing a process 110 for manufacturing trifluoroiodomethane from any of the trifluoroacetyl iodide compositions described above. A feed stream 132 including any of the trifluoroacetyl iodide compositions described above is provided to a vapor-phase reactor 140, as shown in FIG. 2. The trifluoroacetyl iodide reacts at a reaction temperature within the reactor 140 to produce a product stream 144. The product stream 144 comprises trifluoroiodomethane and reaction by-product carbon monoxide according to Equation 1 above.

The reaction temperature may be as low as about 200° C., about 250° C., about 300° C., about 310° C., about 320° C., about 325° C., about 330° C., about 340° C., about 350° C., or about 360° C., or as high as about 370° C., about 380° C., about 390° C., about 400° C., about 425° C., about 450° C., about 475° C., about 500° C., about 525° C., about 550° C., about 575° C., about 600° C., about 700° C. or about 800° C., or any range defined between any two of the foregoing values, such as about 200° C. to about 800° C., about 250° C. to about 600° C., about 300° C. to about 500° C., about 320° C. to about 450° C., about 325° C. to about 400° C., about 330° C. to about 390° C., about 340° C. to about 380° C., about 350° C. to about 370° C., or about 350° C. to about 450° C., for example. Preferably, the reaction temperature is from about 300° C. to about 500° C. More preferably, the reaction temperature is from about 350° C. to about 450° C. Most preferably, the reaction temperature is from about 375° C. to about 425° C.

The reaction may take place in the presence of a catalyst 142 contained within the reactor 140. The catalyst 142 may comprise stainless steel, nickel, nickel-chromium alloy, nickel-chromium-molybdenum alloy, nickel-copper alloy, copper, alumina, silicon carbide, platinum, palladium, rhenium, activated carbon, such as such as Norit-PK35, Calgon or Shirasagi carbon, or combinations thereof. Alternatively or additionally, the surfaces of the reactor 140 itself in contact with the trifluoroacetyl iodide compositions may provide the catalytic effect. Alternatively or additionally, the reaction may proceed by pyrolysis, or thermal decomposition, of the trifluoroacetyl iodide.

The reaction may be conducted at a reaction operating pressure as low as about atmospheric pressure, about 5 psig (34 kPaG), about 10 psig (69 kPaG), about 15 psig (103 kPaG), about 20 psig (138 kPaG), about 25 psig (172 kPaG), about 30 psig (207 kPaG), about 35 psig (241 kPaG), about 40 psig (276 kPaG) or about 50 psig (345 kPaG), or as high as about 60 psig (414 kPaG), about 70 psig (483 kPaG), about 80 psig (552 kPaG), about 100 psig (689 kPaG), about 120 psig (827 kPaG), about 150 psig (1,034 kPaG), about 200 psig (1,379 kPaG), 225 psig (1551 kPaG), about 250 psig (1,724 kPaG), about 275 psig (1896 kPaG), or about 300 psig (2,068 KPaG), or within any range defined between any two of the foregoing values, such as about atmospheric pressure to about 300 psig (2,068 KPaG), about 5 psig (34 kPaG) to about 300 psig (2,068 KPaG), about 5 psig (34 kPaG) to about 250 psig (1,724 kPaG), about 10 psig (69 kPaG) to about 200 psig (1,379 kPaG), about 15 psig (103 kPaG) to about 150 psig (1,034 kPaG), about 20 psig (138 kPaG) to about 120 psig (827 kPaG), about 25 psig (172 kPaG) to about 100 psig (689 kPaG), about 30 psig (207 kPaG) to about 80 psig (552 kPaG), about 35 psig (241 kPaG) to about 70 psig (483 kPaG), about 40 psig (276 kPaG) to about 70 psig (483 kPaG), about 50 psig (345 kPaG) to about 60 psig (414 kPaG), 50 psig (345 kPaG) to about 250 psig (1,724 kPaG), about 100 psig (689 kPaG) to about 200 psig (1,379 kPaG), or about 150 psig (1,034 kPaG) to about 200 psig (1,379 kPaG), for example. Preferably, the reaction is conducted at a reaction operating pressure from about 5 psig (34 kPaG) to about 275 psig (1896 kPaG). More preferably, the reaction is conducted at a reaction operating pressure from about 10 psig (69 kPaG) to about to about 250 psig (1,724 kPaG). Most preferably, the reaction is conducted at a reaction operating pressure from about 20 psig (138 kPaG) to about 225 psig (1551 kPaG).

The trifluoroacetyl iodide composition may be in contact with the catalyst 142 (and/or the surface of the reactor 140) for a contact time as short as about 0.01 second, about 0.05 second, about 0.1 second, about 1 second, about 2 seconds, about 3 seconds, about 5 seconds, about 8 seconds, about 10 seconds, about 12 seconds, or about 15 seconds, or as long as about 18 seconds, 20 seconds, about 25 seconds, about 30 seconds, about 35 seconds, about 40 seconds, about 50 seconds, about 60 seconds, about 300 seconds, or about 600 seconds, or for any contact time within any range defined between any two of the foregoing values, such as about 0.01 seconds to about 600 seconds, about 0.1 seconds to about 600 seconds, about 1 second to about 60 seconds, about 3 seconds to about 50 seconds, about 5 seconds to about 40 seconds, about 8 seconds to about 35 seconds, about 10 seconds to about 30 seconds, about 12 seconds to about 25 seconds, about 15 seconds to about 20 seconds, about 20 seconds to about 25 seconds, about 10 seconds to about 40 seconds, or about 10 seconds to about 30 seconds, for example. Preferably, the trifluoroacetyl iodide composition is in contact with the catalyst 142 (and/or the surface of the reactor 140) for a contact time from about 0.1 seconds to about 100 seconds. More preferably, the trifluoroacetyl iodide composition is in contact with the catalyst 142 (and/or the surface of the reactor 140) for a contact time from about 0.1 second to about 60 seconds. Most preferably, the trifluoroacetyl iodide composition is in contact with the catalyst 142 (and/or the surface of the reactor 140) for a contact time from about 0.1 second to about 10 seconds.

The product stream 144 may proceed directly to a distillation column 146, as shown in FIG. 2. In addition to the trifluoroiodomethane and carbon monoxide, the product stream 144 comprises unreacted trifluoroacetyl iodide and other by-products, such as trifluoromethane ($CHF_3$), hexafluoroethane ($C_2F_6$), and hexafluoroacetone (($CF_3$)$_2CO$). The distillation column 146 is configured for the separation of unreacted trifluoroacetyl iodide and by-products, such as carbon monoxide, trifluoromethane and hexafluoroethane, from the trifluoroiodomethane to produce a purified product stream 148, comprising trifluoroiodomethane. As shown in FIG. 2, the distillation column 146 may be configured to separate and return the unreacted trifluoroacetyl iodide to the feed stream 132 in an unreacted trifluoroacetyl iodide flow 150. The distillation column 146 may also be configured to separate the carbon monoxide into a carbon monoxide stream 152 for sale, reuse elsewhere, or disposal.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" is also considered as disclosing the range defined by the absolute values of the two endpoints.

EXAMPLES

Manufacture of Trifluoroiodomethane from Trifluoroacetyl Iodide Compositions According to Equation 1

In this Example, the successful manufacture of trifluoroiodomethane from trifluoroacetyl iodide compositions according to this disclosure is demonstrated. A unit comprising the operations described above in FIG. 2 was operated for 1,894 hours. Seven samples of the trifluoroacetyl iodide composition used to feed the reactor were obtained and analyzed for organic composition and for inorganic composition. The results are shown in Tables 1 and 2 below, respectively. Table 1 shows the organic composition of each sample as GC area %. Table 2 shows the inorganic composition of each sample in weight percentages of the trifluoroacetyl iodide composition. Each of the trifluoroacetyl iodide compositions produced an acceptable trifluoroiodomethane product.

TABLE 1

| Component | Sample No. | | | | | | |
|---|---|---|---|---|---|---|---|
| | 1 | 2 | 3 | 4 | 5 | 6 | 7 |
| Trifluoroacetyl iodide | 97.6 | 99.4 | 97.1 | 95.7 | 98.2 | 99.2 | 98.7 |
| Methyl propane | 0 | 0.0111 | 0.009 | 0 | 0.0082 | 0.0067 | 0.0223 |
| Trifluoroacetyl fluoride | 0.0006 | 0 | 0.0015 | 0.002 | 0.0034 | 0.001 | 0.0023 |
| Trifluoroacetyl chloride | 0.2676 | 0.0131 | 0.4284 | 0.3534 | 0.0271 | 0.1348 | 0.2831 |
| Trifluoroacetic anhydride | 0.3651 | 0.0421 | 0.0022 | 0.5559 | 0.0276 | 0 | 0 |
| Chlorotrifluoroethane | 0.0339 | 0.0013 | 0.0341 | 0.0213 | 0 | 0.0192 | 0.0129 |
| Trichlorotrifluoroethane | 0 | 0.0158 | 0 | 0 | 0.0031 | 0 | 0 |
| Trifluoroiodomethane | 0.9862 | 0.0406 | 0.0145 | 0.2659 | 0.0091 | 0.0059 | 0.0409 |
| Pentafluoroiodoethane | 0.0348 | 0.0019 | 0 | 0.0355 | 0 | 0 | 0 |
| Methyl trifluoroacetate | 0 | 0 | 0.7482 | 1.7663 | 0.9107 | 0 | 0.0258 |
| Iodomethane | 0.0277 | 0.0159 | 0.0519 | 0.0877 | 0.0321 | 0.0088 | 0.0269 |
| Trifluoroacetic acid | 0.606 | 0.3678 | 0.7870 | 0.676 | 0.5034 | 0.3388 | 0.6374 |
| Others[1] | 0.056 | 0.138 | 0.8310 | 0.545 | 0.259 | 0.312 | 0.293 |

[1]Includes dichlorotetrafluoroethane, difluoroiodomethane, dichlorotrifluoroethane, difluorobutane and iodopropane and other organic impurities.

TABLE 2

| Component | Sample No. | | | | | | |
|---|---|---|---|---|---|---|---|
| | 1 | 2 | 3 | 4 | 5 | 6 | 7 |
| $I_2$ | 0.222 | 0.102 | 0.276 | 0.255 | 0.073 | 0.141 | 0.163 |
| HI | 0 | 0 | 0.290 | 0 | 0.004 | 0.001 | 0.001 |
| $HI_3$ | 0.103 | 0 | 0.027 | 0.056 | 0.051 | 0.081 | 0.055 |
| Others[2] | | | | | | | |

[2]Includes hydrogen chloride, but not measured.

ASPECTS

Aspect 1 is a composition comprising trifluoroacetyl iodide, at least one organic impurity and at least one inorganic impurity. The at least one organic impurity comprises at least one of: difluoroiodomethane, pentafluoroiodoethane, iodomethane, iodopropane, dichlorotetrafluoroethane, dichlorotrifluoroethane, trichlorotrifluoroethane, methyltrifluoroacetate, trifluoroacetic anhydride, difluorobutane and methyl propane. The at least one inorganic impurity comprises at least one of: hydrogen iodide, hydrogen chloride, iodine and hydrogen triiodide.

Aspect 2 is the composition of Aspect 1, wherein the at least one organic impurity is present, in GC area % of total organic compounds, in an amount from about 0.05 GC area % to about 5.0 GC area %.

Aspect 3 is the composition of Aspect 1, wherein the at least one organic impurity is present, in GC area % of total organic compounds, in an amount from about 0.05 GC area % to about 2.0 GC area %.

Aspect 4 is the composition of Aspect 1, wherein the at least one organic impurity is present, in GC area % of total organic compounds, in an amount from about 0.05 GC area % to about 1.0 GC area %.

Aspect 5 is composition of any of Aspects 1-4, wherein the at least one organic impurity comprises trifluoroacetic anhydride present, in GC area % of total organic compounds, in amount from about 0.001 GC area % to about 1.0 GC area %.

Aspect 6 is the composition of any of Aspects 1-5, wherein the at least one organic impurity comprises pentafluoroiodoethane present, in GC area % of total organic compounds, in amount from about 0.0001 GC area % to about 0.5 GC area %.

Aspect 7 is the composition of any of Aspects 1-6, wherein the at least one organic impurity comprises iodomethane present, in GC area % of total organic compounds, in amount from about 0.0001 GC area % to about 0.5 GC area %.

Aspect 8 is the composition of any of Aspects 1-7, wherein the at least one organic impurity comprises methyltrifluoroacetate present, in GC area % of total organic compounds, in amount from about 0.001 GC area % to about 2.0 GC area %.

Aspect 9 is the composition of any of Aspects 1-8, wherein the at least one organic impurity comprises at least one of: difluoroiodomethane, dichlorotetrafluoroethane, dichlorotrifluoroethane, trichlorotrifluoroethane, iodopropane, difluorobutane and methyl propane present, in GC area % of total organic compounds, in total in an amount from about 0.0001 GC area % to about 0.5 GC area %.

Aspect 10 is the composition of any of Aspects 1-9, further comprising at least one additional organic impurity comprising at least one of: trifluoroacetic acid, trifluoroacetyl fluoride, trifluoroacetyl chloride, trifluoroiodomethane and chlorotrifluoroethane.

Aspect 11 is the composition of Aspect 10, wherein the at least one additional organic impurity comprises trifluoroacetic acid present, in GC area % of total organic compounds, in amount from about 0.001 GC area % to about 2.0 GC area %.

Aspect 12 is the composition of Aspect 10 or Aspect 11, the at least one additional organic impurity comprises trifluoroacetyl fluoride present, in GC area % of total organic compounds, in amount from about 0.0001 GC area % to about 0.05 GC area %.

Aspect 13 is the composition of any of Aspects 10-12, wherein the at least one additional organic impurity comprises trifluoroacetyl chloride present, in GC area % of total organic compounds, in amount from about 0.001 GC area % to about 2.0 GC area %.

Aspect 14 is the composition of any of Aspects 10-13, wherein the at least one additional organic impurity comprises trifluoroiodomethane present, in GC area % of total organic compounds, in amount from about 0.0001 GC area % to about 2.0 GC area %.

Aspect 15 is the composition of any of Aspects 10-14, wherein the at least one additional organic impurity comprises chlorotrifluoroethane present, in GC area % of total organic compounds, in amount from about 0.0001 GC area % to about 0.5 GC area %.

Aspect 16 is the composition of any of Aspects 1-15, wherein the at least one inorganic impurity is present in total in an amount from about 0.01 wt. % to about 1.5 wt. % of the composition.

Aspect 17 is the composition of any of Aspects 1-15, wherein the at least one inorganic impurity is present in total in an amount from about 0.01 wt. % to about 0.5 wt. % of the composition.

Aspect 18 is the composition of any of Aspects 1-17, wherein the at least one inorganic impurity comprises iodine in amount from about 0.001 wt. % to about 0.5 wt. % of the composition.

Aspect 19 is the composition of any of Aspects 1-18, wherein the at least one inorganic impurity comprises hydrogen iodide in amount from about 0.0001 wt. % to about 0.5 wt. % of the composition.

Aspect 20 is the composition of any of Aspects 1-18, wherein the at least one inorganic impurity comprises hydrogen triiodide in amount from about 0.0001 wt. % to about 0.5 wt. % of the composition.

Aspect 21 is composition of any of claims 1-19, wherein the at least one organic impurity is present, in GC area % of total organic compounds, in an amount from about 0.05 GC area % to about 5.0 GC area %, and the at least one inorganic impurity is present in an amount from about 0.01 wt. % to about 0.5 wt. % of the composition.

What is claimed is:
1. A composition comprising:
   trifluoroacetyl iodide;
   at least one organic impurity comprising at least one of: iodopropane, dichlorotetrafluoroethane, dichlorotrifluoroethane, trichlorotrifluoroethane, methyltrifluoroacetate, difluorobutane and methyl propane; and
   at least one inorganic impurity comprising at least one of: hydrogen iodide, hydrogen chloride, iodine and hydrogen triiodide.

2. The composition of claim 1, wherein the at least one organic impurity is present, in GC area % of total organic compounds, in an amount from about 0.05 GC area % to about 1.0 GC area %.

3. The composition of claim 1, wherein the at least one organic impurity is present, in GC area % of total organic compounds, in an amount from about 0.05 GC area % to about 0.5 GC area %.

4. The composition of claim 1, wherein the at least one organic impurity comprises methyl propane present, in GC area % of total organic compounds, in an amount from about 0.0001 GC area % to about 0.2 GC area %.

5. The composition of claim 1, wherein the at least one organic impurity comprises methyl propane present, in GC area % of total organic compounds, in an amount from about 0.0001 GC area % to about 0.1 GC area %.

6. The composition of claim 1, wherein the at least one organic impurity comprises methyl propane present, in GC area % of total organic compounds, in an amount from about 0.0001 GC area % to about 0.05 GC area %.

7. The composition of claim 1, wherein the at least one organic impurity comprises at least one of: dichlorotetrafluoroethane, dichlorotrifluoroethane, trichlorotrifluoroethane, iodopropane, difluorobutane and methyl propane present, in GC area % of total organic compounds, in total in an amount from about 0.0001 GC area % to about 0.5 GC area %.

8. The composition of claim 1, further comprising at least one additional organic impurity comprising at least one of: trifluoroacetic acid, trifluoroacetyl fluoride, trifluoroacetyl chloride, trifluoroiodomethane and chlorotrifluoroethane.

9. The composition of claim 8, wherein the at least one additional organic impurity comprises trifluoroacetic acid present, in GC area % of total organic compounds, in amount from about 0.001 GC area % to about 0.1 GC area %.

10. The composition of claim 8, wherein the at least one additional organic impurity comprises trifluoroacetyl fluoride present, in GC area % of total organic compounds, in amount from about 0.0001 GC area % to about 0.05 GC area %.

11. The composition of claim 8, wherein the at least one additional organic impurity comprises trifluoroacetyl chloride present, in GC area % of total organic compounds, in amount from about 0.001 GC area % to about 0.1 GC area %.

12. The composition of claim 8, wherein the at least one additional organic impurity comprises trifluoroiodomethane present, in GC area % of total organic compounds, in amount from about 0.0001 GC area % to about 0.1 GC area %.

13. The composition of claim 8, wherein the at least one additional organic impurity comprises chlorotrifluoroethane present, in GC area % of total organic compounds, in amount from about 0.0001 GC area % to about 0.05 GC area %.

14. The composition of claim 1, wherein the at least one inorganic impurity is present in total in an amount from about 0.01 wt. % to about 0.5 wt. % of the composition.

15. The composition of claim 1, wherein the at least one inorganic impurity is present in total in an amount from about 0.01 wt. % to about 0.2 wt. % of the composition.

16. The composition of claim 1, wherein the at least one inorganic impurity comprises iodine in amount from about 0.001 wt. % to about 0.05 wt. % of the composition.

17. The composition of claim 1, wherein the at least one inorganic impurity comprises hydrogen iodide in amount from about 0.0001 wt. % to about 0.01 wt. % of the composition.

18. The composition of claim 1, wherein the at least one inorganic impurity comprises hydrogen triiodide in amount from about 0.0001 wt. % to about 0.01 wt. % of the composition.

19. The composition of claim 1, wherein the at least one organic impurity is present, in GC area % of total organic compounds, in an amount from about 0.05 GC area % to about 1.0 GC area %, and the at least one inorganic impurity is present in an amount from about 0.01 wt. % to about 0.5 wt. % of the composition.

20. The composition of claim 1, wherein the at least one organic impurity comprises methyl propane, and the at least one inorganic impurity comprises iodine.

21. The composition of claim 1, wherein the at least one organic impurity comprises methyl propane, and the at least one inorganic impurity comprises hydrogen triiodide.

22. The composition of claim 1, wherein the at least one organic impurity comprises at least one of dichlorotetrafluoroethane, dichlorotrifluoroethane and difluorobutane, and the at least one inorganic impurity comprises iodine.

23. The composition of claim 1, wherein the at least one organic impurity comprises at least one of dichlorotetrafluoroethane, dichlorotrifluoroethane and difluorobutane, and the at least one inorganic impurity comprises hydrogen triiodide.

24. The composition of claim 8, wherein the at least one organic impurity comprises trifluoroacetyl chloride, and the at least one inorganic impurity comprises iodine.

25. The composition of claim 8, wherein the at least one organic impurity comprises trifluoroacetyl chloride, and the at least one inorganic impurity comprises hydrogen triiodide.

26. The composition of claim 8, wherein the at least one organic impurity comprises trifluoroacetic acid, and the at least one inorganic impurity comprises iodine.

27. The composition of claim 8, wherein the at least one organic impurity comprises trifluoroacetic acid, and the at least one inorganic impurity comprises hydrogen triiodide.

* * * * *